United States Patent [19]

Watson et al.

[11] 4,157,384

[45] Jun. 5, 1979

[54] COMPOSITIONS HAVING A PHYSIOLOGICAL COOLING EFFECT

[75] Inventors: Hugh R. Watson, Wargrave; David G. Rowsell, Staines; John H. D. Browning, Wokingham, all of England

[73] Assignee: Wilkinson Sword Limited, London, England

[21] Appl. No.: 837,900

[22] Filed: Sep. 29, 1977

Related U.S. Application Data

[60] Division of Ser. No. 486,675, Jul. 8, 1974, abandoned, which is a continuation-in-part of Ser. No. 221,753, Jan. 28, 1972, abandoned.

[51] Int. Cl.² .......................... A61K 7/16; A61K 31/19
[52] U.S. Cl. .......................................... 424/45; 252/32; 252/522; 424/48; 424/49; 424/57; 424/65; 424/73; 424/278; 424/305; 424/307; 424/317; 426/3; 426/590; 426/660

[58] Field of Search ................. 424/305, 307, 317, 49, 424/45

[56] References Cited

U.S. PATENT DOCUMENTS 4,033,994   7/1977   Watson et al. ................... 260/468 R

OTHER PUBLICATIONS

Chemical Abstracts 72:90648f (1970).

*Primary Examiner*—Leonard Schenkman
*Attorney, Agent, or Firm*—Leydig, Voit, Osann, Mayer & Holt, Ltd.

[57] ABSTRACT

Derivatives of p-menthane are disclosed having the property of stimulating the cold receptors of the nervous system of the human body to produce a cold sensation and are used for this purpose in a variety of edible and topical preparations.

15 Claims, No Drawings

COMPOSITIONS HAVING A PHYSIOLOGICAL COOLING EFFECT

RELATED APPLICATIONS This is a division of application Ser. No. 486,675, filed July 8, 1974, now abandoned, which is a continuation-in-part of application Ser. No. 221,753, now abandoned. It is also related to applications Ser. Nos. 486,651 now U.S. Pat. No. 4,059,188 and 486,652 now U.S. Pat. No. 4,033,994.

FIELD OF INVENTION

This invention relates to compositions and compounds having a physiological cooling effect on the skin and on the mucous membranes of the body, particularly those of the mouth, nose, throat and gastrointestinal tract.

BACKGROUND OF THE INVENTION AND PRIOR ART

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producting a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

A few other compounds have been reported in the technical literature as having an odour or flavour similar to menthol and from time to time have been proposed as flavourants or odourants in a variety of topical and ingestible compositions. For example, Japanese Patent Publication No. 39-19627 reports that 3-hydroxymethyl p-menthane (menthyl carbinol) has a flavour closely resembling that of 1-menthol and suggests its use as a flavourant in confectionery, chewing gum and tobacco. In Swiss Pat. No. 484,032 certain saccharide esters of menthol are proposed as additive to tobacco. In French Pat. No. 1,572,332 N,N-Dimethyl 2-ethylbutanamide is reported as having a minty odour and refreshing effect, and the minty odour of N,N-diethyl 2,2-dimethylpropanamide is referred to. A similar effect is reported for N,N-diethyl 2-ethylbutanamide in Berichte 39, 1223, (1906). A minty odour has also been reported for 2,4,6-trimethylheptan-4-ol and 2,4,6-trimethyl hept-2-en-4-ol in Parfums-Cosmetiques-Savons, May 1956, pp. 17–20. The cooling effect of menthol and other related terpene alcohols and their derivatives has also been studied and reported in Koryo, 95, (1970), pp. 39–43. 2,3-p-menthane diol has also been reported as having a sharp cooling taste (Beilstein, Handbuch der Organischen Chemie, 4th Ed. (1923) Vol. 6, p. 744.).

Despite this knowledge of other compounds having an odour and flavour similar to that of menthol, menthol is still extensively used in topical, ingestible and other compositions notwithstanding the disadvantages mentioned above, namely its very strong odour and its relative volatility.

OBJECTS OF THE INVENTION

It is an object of the present invention to provide other compounds having a pronounced physiological cooling effect, in many cases far more persistent than that obtained with menthol, without the attendant disadvantages of a strong odour.

It is a further object to provide compounds having a pronounced physiological cooling effect and being of relatively low volatility.

It is a further object of the present invention to provide ingestible, topical and other compositions capable of stimulating the cold receptors of the nervous system of the human body thereby to create a desirable "cool" sensation, and a method of making them.

It is a yet further object of the present invention to provide a method of stimulating the cold receptors of the nervous system of the body to create a cool sensation.

Other objects will be apparent from the following detailed description of the invention.

SUMMARY OF INVENTION

The present invention is based on the discovery of a group of 3-substituted-p-menthanes which have a pronounced physiological cooling activity, which have little or no odour, which are of relatively low volatility and which are substantially non-toxic. These compounds are 3-substituted-p-menthanes of the formula:

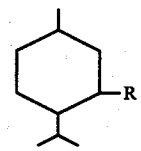

where: R is (i) —CONH$_2$; or (ii) —COOR', where R' is hydrogen; an alkali (eg. Na, K etc) or alkaline earth (eg. Ca, Mg etc) metal atom, or an ammonium or substituted ammonium radical (e.g. trimethylammonium, β-hydroxyethylammonium); or a radical containing from 2 to 10 carbon atoms and selected from hydroxyaliphatic radicals having a hydroxyl substituent in a 2- or 3-position and a hydrogen atom in the 1-position; a lower alkylene oxide (e.g. ethylene oxide, propylene oxide etc) adduct of such a hydroxyaliphatic radical; a ketal derivative of such a hydroxyaliphatic radical with a lower ketone (e.g. acetone); a lower acyl (e.g. acetyl) derivative of such a hydroxyaliphatic radical; a hydroxyaryl radical having a hydroxyl substituent in a 2- or 3-position relative to the ester grouping; a carboxyaliphatic radical having a carboxyl group in a 1-, 2- or 3-position; an alkali metal (e.g. Na, K), alkaline earth metal (e.g. Ca, Mg), ammonium or substituted ammonium (e.g. trimethylammonium, β-hydroxyethylammonium) salt of such a carboxyaliphatic radical; or a lower alkyl (e.g. methyl, ethyl etc.) ester of such a carboxyaliphatic radical.

DEFINITIONS

By 'hydroxyaliphatic' we mean a hydrocarbyl group free of aromatic unsaturation, having a hydroxyl group in the specified position relative to the ester (—COO—) grouping, but being otherwise essentially free of functional groups. Hydroxyaliphatic therefore embraces hydroxyalkyl, hydroxycycloalkyl, hydroxyalkenyl, hydroxyalkynyl, hydroxyalkylcycloalkyl and hydroxycycloalkylalkyl and similar combinations. Particular hydroxyaliphatic groups include 2-hydroxyethyl, 2-hydroxypropyl, 2,3-dihydroxypropyl, sorbityl, 2-hydroxycyclohexyl, 2-hydroxycyclohexylmethyl, 2-hydroxy-4-methylcyclohexyl, 2-hydroxy-1,2-dimethylethyl, and 2-hydroxy-1-methylethyl etc.

By 'carboxyaliphatic' we mean a hydrocarbyl group free of aromatic unsaturation, having a carboxyl group in the specified position relative to the ester (—COO—) grouping but being otherwise essentially free of functional groups. Carboxyaliphatic therefore includes carboxyalkyl, carboxycycloalkyl, carboxyalkenyl, carboxyalkynyl, carboxyalkylcycloalkyl, carboxycycloalkylalkyl and similar combinations. Typical carboxyaliphatic groups include 1-carboxyethyl, 2-carboxyethyl, 2-carboxypropyl, 3-carboxypropyl, 3-carboxypropenyl, 3-carboxypropynyl, 2-carboxycyclohexyl, 2-carboxycyclohexylmethyl, 4-methyl-2-carboxycyclohexyl etc.

By 'hydroxyaryl' we mean a hydrocarbyl group containing aromatic unsaturation, having a hydroxyl group in the specified position relative to the ester (—COO—) grouping, but being otherwise essentially free of functional groups. Hydroxyaryl therefore includes aralkyl, alkaryl and like combinations. As indicated, the hydroxyaryl group will contain a hydroxyl group in a 2- or 3-position relative to the ester grouping; this may be a nuclear hydroxyl group as in ortho-hydroxybenzyl, orthohydroxyphenyl or orthohydroxynaphthyl or in a side chain as in 1-phenyl-2-hydroxyethyl or o-(hydroxymethyl) phenyl.

By 'substituted ammonium' in all instances we mean salts with organic amines, and in particular alkylamines e.g. mono-, di- and trialkylamines and alkanolamines e.g. ethanolamine.

By 'lower' in all instances we mean containing from 1–4 carbon atoms.

By 'essentially free' of functional groups in all instances we mean free of substituent groups such as amino, alkylamino, alkoxy, acyloxy in positions which interfere with the physiological cooling activity.

STATEMENT OF INVENTION

In accordance with this invention, therefore, there are provided consumer products for application to or consumption by the human body comprising a consumer product base and a means for stimulating the cold receptors of the nervous system of the human body wherein said means comprise an effective amount of one or more 3-substituted-p-menthanes of the formula hereinbefore set forth.

By consumer product we mean a manufactured product applied to or consumed by the human person for toilet, cosmetic, hygienic, nutritive, curative, prophylactic, or other purposes and constituting a vehicle by means of which the said 3-substituted-p-menthane may be brought into contact with the skin, mucous membranes or other surface tissues of the body, whether external tissues or internal, for example, of the nose, throat, mouth and gastrointestinal tract, and includes liquid and solid phase preparations of an essentially formless nature e.g. solutions, emulsions, pastes, ointments, powders etc., solid phase preparations of semipermanent form, e.g. shaped toilet and cosmetic preparations and shaped edible preparations, whose shaped form is only temporary and which lose that form on use, and articles of permanent form but which are of an essentially disposable nature, e.g. cleansing tissues, toothpicks etc.

Typical consumer products into which the 3-substituted-p-methanes may be incorporated in accordance with this invention and which may therefore serve as vehicles for application of the compounds to the person are:

1. Edible and potable compositions including alcoholic and non-alcoholic beverages; confectionery; chewing gum; cachous; ice cream; jellies; 2. Toiletries including after-shave lotions, shaving soaps, creams and foams, toilet water, deodorants and antiperspirants, "solid colognes", toilet soaps, bath oils and salts, shampoos, hair oils, talcum powders, face creams, hand creams, sunburn lotions, cleansing tissues, dentifrices, toothpicks, mouthwashes, hair tonics, eyedrops.

3. Medicaments including antispetic ointments, pile ointments, liniments, lotions, decongestants, counter-irritants, cough mixtures, throat lozenges, antacid and indigestion preparations, oral analgesics;

4. Miscellaneous compositions such as water soluble adhesive compositions for envelopes, postage stamps, adhesive labels etc.

DETAILED DESCRIPTION

The 3-substituted-p-menthanes used as cold receptor stimulants in the consumer products of this invention may be readily prepared by conventional methods. Thus, the p-menthane-3-carboxylic acid and its salts may readily be prepared by carbonation of a Grignard reagent derived from menthol. The carboxylic acid may then readily be converted into its acid chloride, for example, by reaction with thionyl chloride, and the acid chloride converted into the amide or an ester derivative by reaction with ammonia or an appropriate alcohol. Other methods for the preparation of the acid, the amide or the esters used in this invention will be apparent to those skilled in the art.

The compounds used as cold receptor stimulants in accordance with this invention exhibit both geometric and optical isomerism and, depending on the starting materials and the methods used in their preparation the compounds may be isomerically pure, i.e. consisting of one geometric or optical isomer, or they may be isomeric mixtures, both in the geometric and optical sense.

As is well known, the basic p-menthane structure is a chair-shaped molecule which can exist in cis or trans forms. Substitution of the carboxyl or amide group into the 3-position gives rise to four configurational or geometric isomers depending upon whether the substitution is axially or equatorially into the cis or trans isomer, the four isomers being related as menthol is to neomenthol, isomenthol, and neoisomenthol. In general it is found that in the compounds used in this invention the equatorially substituted derivatives have the greater cooling effect than the axial compounds and are to be preferred.

Substitution of the carboxyl or amide group in the 3-position of the p-menthane structure also gives rise to optical isomerism, each of the above-mentioned four geometric isomers, existing in d, l and dl forms. The physiological cooling effect is found, in most cases, to be greater in the l-form than in d-form, and in some cases substantially greater. The l-acid and derivatives of the l-acid are therefore preferred.

The cooling sensation created by the compounds used in this invention on the skin and mucous membranes, for example, in the mouth, varies both in intensity and longevity from compound to compound.

In general, the preferred compounds are the acid, i.e. the compound where R is COOH; the amide, i.e. where R=CONH$_2$; the 2-hydroxy (lower) alkyl esters, i.e. where R is COOR', with R' being a lower alkyl group with a hydroxy substituent in the 2-position, and particularly the 2-hydroxyethyl ester.

For the purposes of the present disclosure the following test procedure has been devised as a means to identify compounds having a physiological cooling activity in accordance with the present invention and herein referred to as cold receptor stimulants. This test is intended purely as a means for identifying compounds having a physiological cooling activity and useful in the present invention and for giving an indication of the different relative activities of the compounds, as between themselves and as compared with menthol, when applied in a particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purposes of measuring the relative activities of the compounds on another area of the body, for example, the face or forearm, and this will be a useful guide in the choice of compounds to be used in preparations for external topical usage.

It will also be noted that the described test procedure is done on a statistical basis. This is necessary since sensitivity to these compounds will vary not only from compound to compound and from one part of the body to another, but also from one individual to another. Tests of this nature are commonly used in the testing of the organoleptic properties, e.g. taste, smell etc. of organic and inorganic compounds, see Kirk-Othmer: Encyclopedia of Chemical Technology, 2nd.Ed. (1967) Vol. 14 pages 336–344.

Test Procedure

The following test procedure is aimed at determining the minimum quantity of the test compound required to produce a noticeable cooling effect on a person of average sensitivity, this minimum quantity being termed the threshold for that particular compound. The tests are carried out on a selected panel of 6 people of median sensitivity to 1-menthol.

Panel Selection

To select a test panel of average sensitivity the following procedure is used. Known quantities of 1-menthol in solution in petroleum ether (bp. 40–60) are placed on 5 mm. squares of filter paper, whereafter the solvent is allowed to evaporate. A panel of observers is enrolled and asked to place one impregnated square at a time on the tongue and to report on the presence or absence of a cooling effect. The quantity of 1-menthol on each impregnated square is gradually reduced from a value substantially above 0.25 μg, the precise range being immaterial. Conveniently, one starts with squares containing 2.0 μg. 1-menthol, the amount on each successive square being half that of the preceding square, i.e. the second test square will contain 1.0 μg, the third 0.5 μg and so on. Each quantity is tested on the tongue at least 10 times. In this way, the thresholds to cold receptor stimulus by 1-menthol are determined for each individual of the panel, the threshold for each individual being that amount of 1-menthol for which, in a series of not less than 10 test applications, a cooling effect is reported 50% of the time. Six panel members are now selected whose threshold to 1-menthol is in the range 0.1 μg to 10 μg and whose average threshold is approximately 0.25 μg., this select panel being regarded as the test panel of average sensitivity.

Compound Testing

To test the activity of compounds according to this invention, the above procedure is repeated using only the 6 selected panel members of average sensitivity to 1-menthol. The individual thresholds for each test compound on each of the 6 selected panel members are determined and averaged. Those compounds whose average threshold on the select test panel is 100 μg or less are regarded as having cooling activity in accordance with this invention.

Test Results

The following table sets out the relative cooling activities of compounds of the formula defined above when tested according to the foregoing procedure.

| Compound | Threshold (μg) |
|---|---|
| p-menthane-3-carboxylic acid | 4 |
| p-menthane3-carboxylic acid ammonium salt | 5 |
| p-menthane-3-carboxylic acid sodium salt | 4 |
| p-menthane-3-carboxylic acid ethanolamino salt | 6 |
| p-menthane-3-carboxamide | 20 |
| p-menthane-3-carboxylic acid esters where R' equals: | |
| —CH$_2$CH$_2$OH | 1.5 |
| —CH$_2$CH(OH)CH$_2$OH | 1.2 |
| —CH$_2$CH(OH)CH$_3$ } Isomeric mixture —CH(CH$_2$OH)CH$_3$ | 1.4 |
| —CH$_2$(CHOH)$_4$CH$_2$OH | 50 |
| —CH$_2$CH$_2$OCOCH$_3$ | 33 |
| —CH$_2$CH$_2$CH$_2$OH | 7 |
| —CH(CH$_3$)CH(CH$_3$)OH | 3 |
| —CH$_2$CH(OH)n-C$_4$H$_9$ } Isomeric mixture —CH(CH$_2$OH)n-C$_4$H$_9$ | 8 |
| —CH$_2$CH(OH)n-C$_8$H$_{17}$ | 90 |
| —CH$_2$(CHOH)$_2$CH$_2$OH | 50 |
| —CH$_2$CH$_2$(OCH$_2$CH$_2$)$_2$OH | 5 |
| —CH$_2$CH$_2$OCH$_2$CH$_2$OH | 1.0 |
| —CH$_2$CH$_2$(OCH$_2$CH$_2$)$_{2.75}$OH | 15 |
| 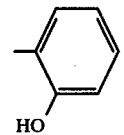 | 5 |
| 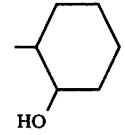 | 4 |

-continued

| Compound | Threshold (μg) |
|---|---|
| [structure: phenol with OH, CH₃ substituents] | 15 |
| —CH₂—CH—CH₂ with O, O bridging to C(CH₃)(CH₃) | 11 |
| —CH(CH₃)COOH | 8 |
| —CH₂CH₂COOH | 10 |
| —C(CH₃)₂COOH | 20 |
| —CH(CH₃)COOC₂H₅ | 50 |
| —CH₂COOH | 15 |

The cold receptor stimulants used in this invention find utility in a wide variety of consumer products for consumption by or application to the human body. Broadly speaking, these products can be divided into ingestibles and topicals, both terms being taken in their broadest possible sense. Thus ingestible is to be taken as including not only foodstuffs and beverages taken into the mouth and swallowed, but also other orally ingested products taken for reasons other than their nutritional value, e.g. indigestion tablets, antacid preparations, laxatives, etc. Ingestible is also to be taken to include edible compositions taken by mouth, but not necessarily swallowed, e.g. chewing gum. Topical is to be taken as including not only compositions such as perfumes, powders and other toiletries, lotions, liniments, oils and ointments, applied to the external surfaces of the human body, whether for medical or other reasons, but also compositions applied to, or which, in normal usuage, come in contact with, internal mucous membranes of the body, such as those of the nose, mouth, or throat, whether by direct or indirect application or inhalation, and thus include nasal and throat sprays, dentifrice, mouthwash and gargle compositions. Topical products, in this context, also include toilet articles such as cleansing tissues and toothpicks.

In formulating the products of this invention the 3-substituted-p-menthane will be incorporated into a vehicle by means of which the compound may be applied to the person. The vehicle may, itself be completely inert or it may, and usually will, contain other active ingredients. A wide variety of vehicles will be suitable, depending upon the particular product involved, such vehicles including solids, liquids, emulsions, foams and gels. Typical vehicles for the 3-substituted-p-methanes include aqueous or alcoholic solutions, oils and fats such as hydrocarbon oils, fatty acid esters, long chain alcohols and silicone oils; finely divided solids such as starch or talc; cellulosic materials such as paper tissue; low-boiling hydrocarbons and halohydrocarbons used as aerosol propellants; gums and natural or synthetic resins.

Generally, these vehicles will contain at least one or more of the following adjuvants: flavourants, colourants, perfuming agents, surface active agents, antiseptic agents, such as are usually employed in topical and ingestible compositions.

A more detailed discussion of particular products according to this invention follows.

Toiletries and Cosmetics

A major area of utility of the 3-substituted-p-menthanes of this invention will be in the field of toilet preparations broadly classed as personal care products. These may be defined as manufactured products applied to the person for the purposes of grooming or hygiene or for cosmetic purposes, including making up and perfumery, but excluding ethical and proprietary medical preparations. Particular personal care products are discussed hereinafter by way of example and are illustrated hereinafter in the specific examples.

One class of personal care product into which the compounds of this invention may be incorporated is represented by lotions for topical application, e.g. after-shave lotions, toilet water etc. where the compound will be used in alcoholic or aqueous alcoholic solution, such solutions usually also containing a perfume or mild antiseptic or both. The amount of compound added to the formulation will usually be in the range 0.5 to 6.0% by weight based on the total composition.

Another class of personal care product is represented by soap and soap-based compositions where the compounds will be used in combination with an oil or fat or a natural or synthetic surfactant e.e. a fatty acid salt or a laurylsulphate salt, the composition usually also containing sn essential oil or perfume. The range of soap compositions will include soaps of all kinds e.g. toilet soaps, shaving soaps, shaving foams etc. particularly shaving foams of the aerosol type. Usually the compound will be added to the formulation in amount of from 2.5 to 8.0% by weight.

A further class of personal care products into which the 3-substituted-p-menthanes may be incorporated is represented by cosmetic creams, emollients and lotions, such creams, emollients and lotions usually comprising an oil-in-water emulsion as a base and optionally containing a range of other ingredients such as wax, preservative, perfume, antiseptics, astringents, pigments etc. Also included within this class are lipstick compositions, such compositions usually comprising an oil and wax base into which the coolant can be incorporated along with other ingredients e.g. pigments. Once again the formulation of such products, apart from the incorporation of the 3-substituted-p-menthane, usually in an amount of from 0.05 to 10% by weight, is conventional.

Personal care products for oral hygiene into which the cold receptor stimulants of this invention can be incorporated include mouthwash, gargle and dentifrice compositions. The first two may be considered together and will usually comprise an aqueous, alcoholic or aqueous-alcoholic solution of an antiseptic often coloured or flavoured for palatability, to which the 3-substituted-p-menthane is added in an amount of from 0.05 to 1.0% by weight.

Dentifrice compositions may be of the solid block, powder, paste or liquid type and will usually comprise a finely divided abrasive or polishing material, e.g. precipitated chalk, silica, magnesium silicate, aluminium hydroxide or other similar materials well known in the art, and a detergent or foaming agent. Optional ingredients which may also be included are flavouring agents and colourants, antiseptics, lubricants, thickeners, emulsifiers or plasticizers. The amount of 3-substituted-p-menthane added in such compositions will generally be from 0.5 to 2.0% by weight based on the total composition.

Edible and Potable Compositions

The 3-substituted-p-menthanes of this invention may be incorporated into a wide range of edible and potable compositions comprising an edible or potable base and usually one or more flavouring or colouring agents. The particular effect of the 3-substituted-p-menthane is to create a cool or fresh sensation in the mouth, and in some cases, even in the stomach, and therefore the compounds find particular utility in sugar-based confectionery such as chocolate, boiled sweets, mints and candy, in ice cream and jellies and in chewing gum. The formulation of such confections will be by traditional techniques and according to conventional recipes and as such forms no part of this invention. The 3-substituted-p-menthane will be added to the recipe at a convenient point and in amount sufficient to produce the desired cooling effect in the final product. As already indicated, the amount will vary depending upon the particular compound, the degree of cooling effect desired and the strength of other flavourants in the recipe. For general guidance, however, amounts in the range 0.05 to 10% by weight based on the total composition will be found suitable.

Similar considerations apply to the formulation of beverages. Generally speaking the compounds will find most utility in soft drinks, e.g. fruit squashes, lemonade, cola etc., but may also be used in alcoholic beverages. The amount of compound used will generally be in the range 0.025 to 5.0% by weight based on the total composition.

Medicaments

Because of their cooling effect on the skin and on the mucous membranes of the mouth, throat and nose and of the gastrointestinal tract the 3-substituted-p-menthanes may be used in a variety of oral medicines, nasal and throat sprays, and topical compositions, particularly where a counter-irritant is required. Generally speaking, these medical preparations, whether topical or ingestible proprietary or ethical, will contain a pharmaceutically acceptable carrier, either liquid or solid, a pharmaceutically active ingredient and into these preparations the 3-substituted-p-menthanes of this invention can readily be incorporated to provide a pleasant cooling effect on the skin, or other surface tissues of the body, or in the mouth or gastrointestinal tract depending on particular preparation and whether it is to be applied externally or internally. A particular utility for the compounds of this invention is in the formulation of antacid and indigestion remedies, and especially those based on sodium bicarbonate, magnesium oxide, calcium or magnesium carbonate, aluminium or magnesium hydroxide or magnesium trisilicate. In such compositions the compound will usually be added in an amount of from 0.05 to 1.0% by weight.

The 3-substituted-p-menthanes may also be included in oral analgesic compositions e.g. with acetyl salicylic acid or its salts, and in nasal decongestants e.g. those containing ephedrine.

Consumer products according to the invention are illustrated by the following Examples in which all percentages are by weight.

EXAMPLE 1

Aerosol Shaving Soap

An aerosol shaving soap composition was formulated according to the following recipe:

| | |
|---|---|
| Stearic acid | 6.3% |
| Lauric acid | 2.7 |
| Triethanolamine | 4.6 |
| Sodium carboxymethyl cellulose | 0.1 |
| Sorbitol | 5.0 |
| Perfume | 0.4 |
| Water | to 100% |

The composition was prepared by fusing the acids in water, adding the triethanolamine, cooling and adding the other constituents. To the mixture was then added 1.0%, based on the total composition of the sodium salt of p-menthane-3-carboxylic acid. The composition was then packaged in an aerosol dispenser under pressure of a butane propellant.

When used in shaving a fresh cool sensation was distinctly noticeable on the face.

EXAMPLE 2

After Shave Lotion

An after shave lotion was prepared according to the following recipe by dissolution of the solid ingredients in the liquid and cooling and filtering:

| | |
|---|---|
| Denatured Ethanol | 75% |
| Diethylphthalate | 1.0% |
| Propylene Glycol | 1.0% |
| Lactic Acid | 1.0% |
| Perfume | 3.0% |
| Water | to 100% |

Into the base lotion was added 2.0% by weight based on the total composition of p-menthane-3-carboxylic acid.

When applied to the face a clearly noticeable cooling effect became apparent after a short interval of time.

EXAMPLE 3

Toilet Water

A toilet water was prepared according to the following recipe;

| | |
|---|---|
| Denatured Ethanol | 75.0% |
| Perfume | 5.0% |
| Water | to 100% |

To the recipe was added 3.0%, based on the total composition, of p-menthane-3-carboxylic acid.

As with the after shave lotion, a cooling effect was clearly noticeable on the skin well after the termination of any cooling effect attributable to the evaporation of the alcoholic carrier.

EXAMPLE 4

Deodorant Composition

A deodorant composition suitable for formulation and dispensing as an aerosol under pressure of a suitable propellant was formulated according to the following recipe:

| | |
|---|---|
| Denatured Ethanol | 96.9% |

| | |
|---|---|
| Hexachlorophene | 2.0% |
| Isopropyl myristate | 1.0% |
| Perfume | 0.1% |

To the composition was added 3.0% by weight of 1-methyl-2-hydroxy-propyl-p-menthane-3-carboxylate. Application of the final composition gave rise to a definite cooling sensation on the skin.

EXAMPLE 5

Hair Shampoo

Sodium lauryl ether sulphate, 10 g., was dispersed in 90 g. water in a high speed mill. To the dispersion was added 2.0% by weight of the sodium salt of p-menthane-3-carboxylic acid. When the hair is washed using the shampoo a fresh, cool sensation is noticed on the scalp.

EXAMPLE 6

Lipstick 0.25% by weight of p-menthane-3-carboxylic acid was incorporated into a proprietary lipstick by melting the lipstick, according the compound, and allowing the lipstick to resolidify. When applied to the lips a persistant cooling effect is clearly noticeable.

EXAMPLE 7

Solid Cologne

A solid cologne was formulated according to the following recipe:

| | |
|---|---|
| Denatured ethanol | 74.5% |
| Propylene glycol | 3.0% |
| Sodium stearate | 5.0% |
| Perfume | 5.0% |
| Water | to 100% |

The sodium stearate was dissolved by stirring in a warm mixture of the ethanol, propylene glycol and water. To the solution was added the perfume and 3.0% of p-menthane-3-carboxylic acid and the mixture then allowed to solidify into a waxy cake.

When applied to the forehead a strong cooling effect is obtained.

EXAMPLE 8

Hair Tonic

A hair tonic was formulated containing:

| | |
|---|---|
| Denatured ethanol | 84.5% |
| Castor Oil | 14.0% |
| Resorcinol | 0.5% |
| Perfume | 1.0% |

The caster oil, resorcinol and perfumes werre dissolved in the ethanol component and to the solution was added 2.0% of 2-hydroxypropyl-p-menthane-3-carboxylate. When rubbed on the scalp a cooling effect is noticed.

EXAMPLE 9

Eye Lotion

An eye lotion was prepared containing the following ingredients:

| | |
|---|---|
| Witch Hazel | 12.95% |
| Boric Acid | 2.00% |
| Sodium Borate | 0.50% |
| Allantoin | 0.05% |
| Salicylic Acid | 0.025% |
| Chlorobutol | 0.02% |
| Zinc Sulphate | 0.004% |
| Water | to 100% |

To the formulation was added 0.002%, based on the total composition of p-menthane-3-carboxylic acid. Bathing the eyes in the final lotion produced a cool sensation in the eyeball and in the eyelids.

EXAMPLE 10

Mouthwash

A concentrated mouthwash composition was prepared according to the following recipe:

| | |
|---|---|
| Ethanol | 3.0% |
| Borax | 2.0% |
| Sodium bicarbonate | 1.0% |
| Glycerol | 10.0% |
| Flavourant | 0.4% |
| Thymol | 0.03% |
| Water | to 100% |

To the composition was added 0.25% of p-menthane-3-carboxylic acid.

When diluted with approximately 10 times its own volume of water and used to rinse the mouth a strong cooling effect is obtained in the mouth.

EXAMPLE 11

Toothpaste

The following ingredients were mixed in a blender:

| | |
|---|---|
| Dicalcium phosphate | 48.0% |
| Sodium lauryl Sulphate | 2.5% |
| Glycerol | 24.8% |
| Sodium carboxymethyl cellulose | 2.0% |
| Citrus flavourant | 1.0% |
| Sodium saccharin | 0.5% |
| Water | to 100% |

Shortly before completion of the blending operation 1.0% by weight of the ammonium salt of p-menthane-3-carboxylic acid was added to the blender.

When applied as a toothpaste, a strong cooling effect is noticed in the mouth.

EXAMPLE 12

Toothpicks

The tip of a wooden toothpick was impregnated with an alcohol solution containing p-menthane-3-carboxylic acid in sufficient amount to deposit on the toothpick 0.05 mg. of the acid. The impregnated toothpick was then dried. When placed on the tongue there is no detectable taste, however, a distinct cooling effect is noticeable after a short period of time.

EXAMPLE 13

Talcum Powder

A talcum powder was prepared by grinding together the following:

| Low micron talc | 90% |
| --- | --- |
| Zinc stearate | 5% |
| Starch | 5% |

In the course of grinding there was added 5.0% of the sodium salt of p-menthane-3-carboxylic acid. A talcum powder having a freshening and cooling effect was obtained.

EXAMPLE 14

Soft Drink

A soft drink concentrate was prepared from the following recipe:

| Pure orange juice | 60% |
| --- | --- |
| Sucrose | 10% |
| Saccharin | 0.2% |
| Orange flavouring | 0.1% |
| Citric acid | 0.2% |
| Sulphur dioxide | trace amount |
| Water | to 100% |

To the concentrate was added 0.1% of p-menthane-3-carboxylic acid.

The concentrate was diluted with water and tasted. An orange flavour having a pleasantly cool after-effect was obtained.

EXAMPLE 15

Alcoholic Beverage p-Menthane-3-carboxylic acid was added to a proprietary gin in an amount of 0.5%. When tasted a strong cooling after-effect is obtained in the mouth.

EXAMPLE 16

Boiled Sweet 99.5% sucrose and 0.5% citric acid were carefully fused together in the presence of a trace of water. Just before casting the melt onto a chilled plate 0.5% of p-menthane-3-carboxylic acid were rapidly stirred in. The melt was then cast. A boiled sweet resulted having a marked cooling effect on the mouth.

EXAMPLE 17

Mint Sweet

Water was added to icing sugar at 40° C. to form a stiff paste. 0.5% of p-menthane-3-carboxylic acid was then stirred into the paste and the mixture allowed to set. A soft sweet mass resulted having the characteristic cooling effect in the mouth of peppermint but without the minty flavour or odour.

EXAMPLE 18

Chewing Gum

Leaves of a proprietary chewing gum were leached in running water for 168 hours to remove all water-soluble flavourants. At the end of the leaching operation the chewing gum base had no detectable minty odour or flavour. The chewing gum base was then kneaded with 0.16% of p-menthane-3-carboxamide. When compared with the water-extracted chewing gum base, the final product showed no distinguishable change in flavour but showed a marked cooling effect in the mouth.

EXAMPLE 19

Ice Cream

A proprietary ice cream mixture was mixed in accordance with the manufacturers instructions. Shortly before freezing p-menthane-3-carboxamide was added in an amount of 0.13%. When sampled a cooling effect is noticeable which persists after the cooling effect attributable to the temperature of the ice cream has disappeared.

EXAMPLE 20

Indigestion Tablet

The following ingredients were ground together:

| Magnesium carbonate | 49.5% |
| --- | --- |
| Sorbitol | 49.4% |
| Saccharin | 0.1% |
| Talc | 1.0% |

Added to the mixture during grinding was 0.5% of p-menthane-3-carboxylic acid. After mixing the mixture was pressed into 0.5 g tablets.

Taken by mouth and swallowed the tablets produces after a short interval of time a noticeable cooling effect in the stomach.

EXAMPLE 21

Antiseptic Ointment

An ointment was prepared according to the following formulation:

| Cetyltrimethyl ammonium bromide | 4.0% |
| --- | --- |
| Cetyl alcohol | 6.0% |
| Stearyl alcohol | 6.0% |
| White Paraffin | 14.0% |
| Mineral Oil | 21.0% |
| Water | to 100% |

The ingredients were mixed, warmed to 40° C. and emulsified in a high speed blender. Added to the mixture during blending was 1.0% p-menthane-3-carboxamide.

The final ointment when applied to the skin gave rise to a marked cooling effect.

EXAMPLE 22

Antipruritic Ointment

The following ingredients were warmed together to form a homogenous melt:

| Methyl salicylate | 50.0 |
| --- | --- |
| White Beeswax | 25.0% |
| Anhydrous lanolin | 25.0% |

To the melt was added 0.3% p-menthane-3-carboxamide and the mixture then allowed to solidify. A soft ointment resulted having a soothing effect on the skin accompanied by a noticeable cooling effect.

EXAMPLE 23

Analgesic Tablet

Soluble aspirin (calcium acetylsalicylate) tablets were impregnated with 0.5% of p-menthane-3-carboxylic acid by absorption in the tablet of a metered drop of an ethanolic solution of the acid. When a tablet was swallowed a quite noticeable cooling effect developed in the stomach after a short interval.

EXAMPLE 24

Cleansing Tissue

A cleansing liquid was prepared having the formulation:

| | |
|---|---|
| Triethanolamine Lauryl Sulphate | 1.0% |
| Glycerol | 2.0% |
| Perfume | .95% |
| Water | to 100% |

To this liquid was added 1.0% of p-menthane-3-carboxamide. A paper tissue was then soaked in the liquid.

When the impregnated tissue was used to wipe the skin a fresh cool sensation developed on the skin after a short interval.

EXAMPLE 25

Water Soluble Adhesive

A 5% solution of Gum Acacia in water was prepared and 0.25% of p-menthane-3-carboxylic acid added thereto. The solution was taken coated on a label and allowed to dry. Licking the adhesive layer to restore tack before applying the label to a substrate produced a pleasant cooling effect on the tongue.

The above Examples illustrate the range of compounds and the range of compositions included within the present invention. However, they are not to be taken as limiting the scope of the invention in any way. Numerous other compounds within the general formula will be equally suitable for use in the compositions of Examples 1-25 and the physiological cooling effect obtained with the compounds of the invention will recommend their use in a wide variety of other compositions where the cooling effect will be of value.

Toxicology and Dermatology

Toxicological studies on the compounds used in this invention have shown that the compounds are substantially non toxic. LD values for mice are in excess of 2 g/kg. Enclosed patch tests on the skin have shown an extremely low level of allergic response even in persons known to be extremely susceptible to skin allergies. Eye tests in rabbits have also shown that the compounds are substantially free of ocular irritancy.

We claim:

1. In a consumer product for application to or consumption by the human body comprising a consumer product base and, as adjuvants in said base, (i) at least one of the following: a flavourant, colourant, perfuming agent, surface active agent, antiseptic or pharmaceutically active agent, and (ii) an ingredient capable of stimulating the cold receptors of the nervous system of the surface tissues of the body in those parts of the human body with which the product comes in contact during use, the improvement which comprises using as the cold receptor stimulating ingredient an effective amount of a cold receptor stimulating compound of the formula:

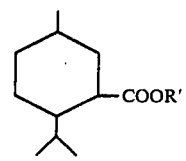

where R' is H or an aliphatic radical of up to 10 carbon atoms selected from: mono- and poly-hydroxyalkyl and cycloalkyl radicals containing from 2 to 10 carbon atoms and having a hydroxyl group in one or more of the 2- and 3-positions and a hydrogen atom in the 1-position; (2,2-dimethyl-1,3-dioxolan-4-yl)methyl; an acylated derivative of a mono- or poly-hydroxyalkyl radical of 2-9 carbon atoms and having a hydroxyl group in a 2- or 3-position and a hydrogen atom in the 1-position with a lower alkanoic acid; aryl hydrocarbon radicals of up to 10 carbon atoms and containing a hydroxyl substituent in a 2- or 3-position relative to the ester grouping; carboxyalkyl radicals containing a carboxyl group in the 1-, 2- or 3-position; an alkali metal, alkaline earth metal, ammonium or ethanolamine salt of such a carboxyalkyl radical; and lower alkyl esters of such carboxyalkyl radicals.

2. A product according to claim 1, wherein said compound is of the formula:

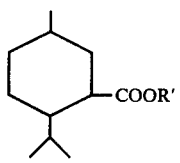

wherein R' is a $C_2-C_4$ hydroxyalkyl group having a hydroxyl group in the 2-position.

3. A product according to claim 1, wherein said compound is 2'-hydroxyethyl p-menthane-3-carboxylate.

4. A product according to claim 1, which is a personal care product comprising a topically administrable base and, as adjuvants in said base, (i) a perfuming agent, a surface active agent or an antiseptic agent, and (ii) said cold receptor stimulant.

5. A product according to claim 1, which is a dentifrice comprising an orally acceptable dentifrice base and, as adjuvants therein, (i) a flavourant or antiseptic, and (ii) said cold receptor simulant.

6. A product according to claim 1, which is a toilet lotion comprising an aqueous, alcoholic or aqueous alcoholic base and, as adjuvants therein, (i) an antiseptic, perfuming agent, colourant or a mixture thereof, and (ii) said cold receptor stimulant.

7. A product according to claim 1, which is a cosmetic preparation comprising an oil-in-water emulsion base, and, as adjuvants in said base, (i) at least one of the following: an antiseptic, perfuming agent or colourant and (ii) said cold receptor stimulant.

8. A product according to claim 1, which is a shaving preparation comprising a foamable base containing a soap or synthetic surfactant and, as adjuvants in said base, (i) a perfume or antiseptic or a mixture thereof and (ii) said cold receptor stimulant.

9. A product according to claim 1, which is an edible preparation comprising an edible base and, as adjuvants in said base, (i) a flavourant and (ii) said cold receptor stimulant.

10. A product according to claim 1, which is a potable preparation comprising a potable base and, as adjuvants in said base, (i) a flavourant and (ii) said cold receptor stimulant.

11. A product according to claim 1, which is a chewing gum containing a chewing gum base and, as adjuvants therein, a flavourant and said cold receptor stimulant.

12. A product according to claim 1, which is a pharmaceutical preparation comprising a pharmaceutically acceptable carrier, and as adjuvants therein, (i) a pharmaceutically active compound and (ii) said cold receptor stimulant.

13. In a consumer product for application to or consumption by the human body comprising a consumer product base and, as adjuvants in said base, (i) at least one of the following: a flavourant, colourant, perfuming agent, surface active agent, antiseptic or pharmaceutically active agent, and (ii) an ingredient capable of stimulating the cold receptors of the nervous system of the surface tissues of the body in those parts of the human body with which the product comes in contact during use, the improvement which comprises using as the cold receptor stimulating ingredient an effective amount of the compound p-menthane-3-carboxylic acid or an alkali metal, alkaline earth metal, ammonium or ethanolamine salt thereof.

14. In a consumer product for application to or consumption by the human body comprising a consumer product base and, as adjuvants in said base, (i) at least one of the following: a flavourant, colourant, perfuming agent, surface active agent, antiseptic or pharmaceutically active agent, and (ii) an ingredient capable of stimulating the cold receptors of the nervous system of the surface tissues of the body in those parts of the human body with which the product comes in contact during use, the improvement which comprises using as the cold receptor stimulating ingredient an effective amount of a cold receptor stimulating compound of the formula:

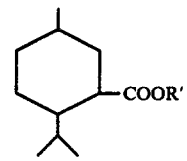

where R' is a radical containing up to 10 carbon atoms, said radical being an adduct of a hydroxyalkyl radical of at least 2 carbon atoms and having a hydroxyl group in the 2- or 3-position and a hydrogen atom in the 1-position, with from 1 to 3 moles of a lower alkylene oxide.

15. A method of stimulating the cold receptors of the nervous system of the human body which comprises applying thereto an effective amount of a cold receptor stimulating compound of the formula defined in claim 1.

* * * * *